(12) United States Patent
Yuan et al.

(10) Patent No.: US 7,253,201 B2
(45) Date of Patent: Aug. 7, 2007

(54) SMALL MOLECULE INHIBITORS OF NECROSIS

(75) Inventors: Junying Yuan, Newton, MA (US); Alexei Degterev, Brighton, MA (US); Timothy J. Mitchison, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/880,377

(22) Filed: Jun. 29, 2004

(65) Prior Publication Data

US 2005/0131044 A1   Jun. 16, 2005

Related U.S. Application Data

(63) Continuation of application No. 09/688,015, filed on Oct. 13, 2000, now Pat. No. 6,756,394.

(60) Provisional application No. 60/174,749, filed on Jan. 6, 2000, provisional application No. 60/159,668, filed on Oct. 15, 1999.

(51) Int. Cl.
*A61K 31/416* (2006.01)

(52) U.S. Cl. ..................................... 514/403
(58) Field of Classification Search ..................... None
See application file for complete search history.

(56) References Cited

U.S. PATENT DOCUMENTS

| | | | |
|---|---|---|---|
| 4,837,165 A | 6/1989 | Hawke | |
| 5,693,643 A | 12/1997 | Gilbert et al. | |
| 5,962,535 A * | 10/1999 | Miyamoto et al. | .......... 514/724 |

FOREIGN PATENT DOCUMENTS

JP           02019363       1/1990

OTHER PUBLICATIONS

Borner and Monney, "Apoptosis without Caspases: An Inefficient Molecular Guillotine?" *Cell Death Differ.* 6:497-507 (1999).
Büyükbingöl et al., "Studies on the Synthesis and Structure-Activity Relationships of 5-(3'-Indolal)-2-Thionydantoin Derivatives as Aldose Reductase Enzyme Inhibitors," *Farmaco*, 49:443-447 (1994).
Chi et al., "Oncogenic Ras Triggers Cell Suicide Through the Activation of a Caspase-Independent Cell Death Program in Human Cancer Cells," *Oncogene* 18:2281-2290 (1999).
Edman, "Method for Determination of the Amino Acid Sequence in Peptides," *Acta Chem. Scand.* 4:283-293 (1950).
Fiers et al., "More Than One Way to Die: Apoptosis, Necrosis and Relative Oxygen Damage," *Oncogene* 18:7719-7730 (1999).
Fujiwara et al., "$^{13}$C Nuclear Magnetic Resonance Studies on the Conformation of Substituted Hydantoins," *J. Chemical Soc. Perkin.* 2:1573-1577 (1980).
Herceg and Wang, "Failure of Poly(ADP-Ribose) Polymerase Cleavage by Caspases Leads to Induction of Necrosis and Enhanced Apoptosis," *Mol. Cell. Biol.* 19:5124-5133 (1999).
Hirsch et al., "The Apoptosis-Necrosis Paradox. Apoptogenic Proteases Activated After Mitochondrial Permeability Transition Determine the Mode of Cell Death," *Oncogene* 15:1573-1581 (1997).
Holler et al., "Fas Triggers an Alternative, Caspase-8-Independent Cell Death Pathway Using the Kinase RIP as Effector Molecule," *Nature Immunol.* 1:489-495 (2000).
Kawahara et al., "Caspase-Independent Cell Killing by Fas-Associated Protein with Death Domain," *J. Cell. Biol.* 143:1353-1360 (1998).
Khwaja and Tatton, "Resistance to the Cytotoxic Effects of Tumor Necrosis Factor Alpha can be Overcome by Inhibition of a FADD/Caspase-Dependent Signaling Pathway," *J. Biol. Chem.* 274:36817-23 (1999).
Kitanaka and Kuchino, "Caspase-Independent Programmed Cell Death with Necrotic Morphology," *Cell Death Differ.* 6:508-515 (1999).
Leist et al., "Inhibition of Mitochondrial ATP Generation by Nitric Oxide Switches Apoptosis to Necrosis," *Exp. Cell Res.* 249:396-403 (1999).
Li and Beg, "Induction of Necrotic-Like Cell Death by Tumor Necrosis Factor Alpha and Caspase Inhibitors: Novel Mechanism for Killing Virus-Infected Cells," *J. Virol.* 74:7470-7477 (2000).
Lüschen et al., "Sensitization to Death Receptor Cytotoxicity by Inhibition of Fas-Associated Death Domain Protein (FADD)/Caspase Signaling. Requirement of Cell Cycle Progression," *J. Biol. Chem.* 275:24670-24678 (2000).
Matsumura et al., "Necrotic Death Pathway in Fas Receptor Signaling," *J. Cell. Biol.* 151:1247-1255 (2000).
McCarthy et al., "Inhibition of Ced-3/ICE-Related Proteases Does Not Prevent Cell Death Induced by Oncogenes, DNA Damage, or the Bcl-2 Homologue Bak," *J. Cell. Biol.* 136:215-227 (1997).
Molina et al., "A Simple and General Entry to Aplysinopsine-Type Alkaloids by Tandem Aza-Wittig/Heterocumulene-Mediated Annelation," *Tet. Lett.* 33:4491-4494 (1992).
Sané and Bertrand, "Caspase Inhibition in Camptothecin-Treated U-937 Cells is Coupled with a Shift from Apoptosis to Transient G1 Arrest Followed by Necrotic Cell Death," *Cancer Res.* 59:3565-3569 (1999).
Takahashi et al., "Antimutagenic Properties of 3,5-Disubstituted 2-Thiohydantoins," *J. Agric. Food Chem.* 46:5037-5042 (1998).
Vercammen et al., "Inhibition of Caspases Increases the Sensitivity of L929 Cells to Necrosis Mediated by Tumor Necrosis Factor," *J. Exp. Med.* 187:1477-1485 (1998).
Vercammen et al., "Dual Signaling of the Fas Receptor: Initiation of Both Apoptotic and Necrotic Cell Death Pathways," *J. Exp. Med.* 188:919-930 (1998).
Waterfield and Haber, "Amino Acid Sequence Analysis with Methyl Isothiocyanate Resolution of the Methylthiohydantoins by Gas—Liquid Partition Chromatography," *Biochemistry* 9:832-839 (1970).
Woo, "Gas-Chromatographic Determination of Methylthiogydantoin Amino Acid as N(O)-Butlydimethylsilyl Derivatives in Amino Acid Sequencing with Methylisothiocyanate," *J. Korean Agric. Chem. Soc.* 35:132-138 (1992).
Inglis et al., "The Identification of Tryptophan Residues in Proteins as Oxidized Derivatives During Amino Acid Sequence Determinations," *FEBS Lett.* 104:115-118 (1979) (Abstract).

\* cited by examiner

*Primary Examiner*—Golam Shameem
*Assistant Examiner*—Andrew S. Freistein
(74) *Attorney, Agent, or Firm*—Clark & Elbing LLP; Kristina Bieker-Brady

(57) ABSTRACT

The invention features methods for decreasing necrosis. The invention also features methods for treating a subject with a condition in which necrosis occurs. The invention further features chemical compounds used to decrease necrosis.

7 Claims, 8 Drawing Sheets

SMALL MOLECULE INHIBITORS OF NECROSIS

CROSS REFERENCE TO RELATED APPLICATIONS

This application is a continuation of application Ser. No. 09/688,015, filed Oct. 13, 2000, now U.S. Pat. No. 6,756,394, which claims priority from U.S. Provisional Application Ser. Nos. 60/159,668, filed Oct. 15, 1999 and 60/174,749, filed Jan. 6, 2000. Each of above applications is hereby incorporated by reference in its entirety.

STATEMENT AS TO FEDERALLY SPONSORED RESEARCH

This invention was made in part with Government funding, and the Government therefore has certain rights in the invention.

BACKGROUND OF THE INVENTION

In general, the invention relates to methods and compounds used to decrease necrosis.

In many diseases, cell death is mediated through apoptotic and/or necrotic pathways. While much is known about the mechanisms of action that control apoptosis, control of necrosis is not as well understood. Understanding the mechanisms regulating both necrosis and apoptosis in cells is essential to being able to treat conditions, such as neurodegenerative diseases, stroke, coronary heart disease, kidney disease, and liver disease. A thorough understanding of necrotic and apoptotic cell death pathways is also crucial to treating AIDS and the conditions associated with AIDS, such as retinal necrosis.

Research has shown that caspases play a central role in the induction of apoptosis. Peptide based inhibitors of caspases, such as zVAD-fmk are useful in preventing activation of the apoptotic cell death pathway in cells stimulated to undergo apoptosis by compounds such as TNFα. However, cells treated with zVAD-fmk and these cell death stimuli still die through a caspase-independent form of necrosis.

Discovery of a compound which prevents caspase-independent cell death (necrosis) would provide a useful therapeutic for treating conditions in which necrosis occurs, and for preventing the onset of necrosis. These compounds and methods may be particularly useful for treating ischemic brain and heart injuries and head traumas.

SUMMARY OF THE INVENTION

The present invention features methods and compounds for decreasing necrosis. The compounds of the present invention may be used as therapeutics to decrease necrosis in a desired cell, such as a neuron. These compounds are characterized by their ability to decrease necrosis in response to modulation of intracellular signaling pathways, such as those activated by TNFα. By also treating the cells with zVAD-fmk, we have inhibited the apoptotic pathway. Accordingly, we have been able to determine that the compounds of the invention specifically decrease necrosis. In addition, we have shown that the identified compounds that decrease necrosis in response to a necrotic pathway activated by zVAD-fmk and TNFα, also decrease necrosis in response to a necrotic pathway activated by zVAD-fmk and dimethyl sulfoxide (DMSO).

Accordingly, in a first aspect, the invention features a chemical compound in a pharmaceutically acceptable carrier, having the formula:

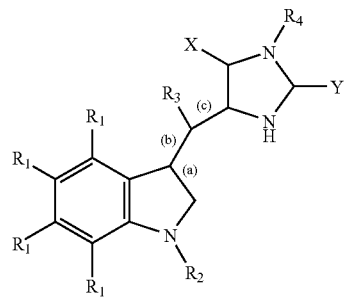

wherein each $R_1$ is independently selected from the group consisting of hydrogen, carboxy, methyl, hydroxyl, methoxyl, amino, and nitro; $R_2$ is selected from the group consisting of hydrogen, alkyl, and acyl; $R_3$ is selected from the group consisting of alkyl, acyl, halogen, hydrogen, or hydroxyl; $R_4$ is selected from the group consisting of methyl, hydroxyl, carboxyl, and linear and branching alkyl groups; X is selected from the group consisting of =O, —OH and —H; Y is selected from the group consisting of =S and —$SR_5$, where $R_5$ is either hydrogen or an alkyl group; and each of the bonds (a), (b), and (c) independently is either a double or single bond, provided, however, that bond (a) and bond (b) are not both double bonds.

In a preferred embodiment of the first aspect of the invention, in the compound each $R_1$ is hydrogen; $R_2$ and $R_3$ are each hydrogen; $R_4$ is a methyl group; X is =O; Y is =S; bond (a) is a double bond; and bonds (b) and (c) are each single bonds.

In another embodiment, the acyl group of $R_1$ or $R_3$ is selected from the group consisting of:

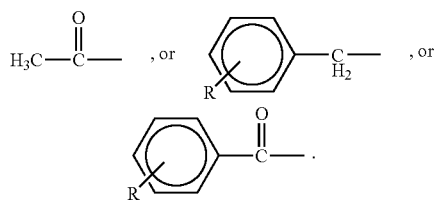

In other embodiments, in the compound if $R_1$ is a hydrogen, then $R_2$ and $R_3$ are not each hydrogen; or $R_4$ is not a methyl group; or X is not =O; or Y is not =S; or bond (a) is not a double bond; or bonds (b) and (c) are not each single bonds. If $R_2$ is a hydrogen, then $R_1$ is a not a hydrogen, or $R_3$ is not a hydrogen; or $R_4$ is not a methyl group; or X is not =O; or Y is not =S; or bond (a) is not a double bond; or bonds (b) and (c) are not each single bonds. If $R_3$ is a hydrogen, then $R_1$ is a not a hydrogen, or $R_2$ is not a hydrogen; or $R_4$ is not a methyl group; or X is not =O; or Y is not =S; or bond (a) is not a double bond; or bonds (b) and (c) are not each single bonds. If $R_4$ is a methyl group, then $R_1$ is a not a hydrogen, or $R_2$ and $R_3$ are not each not a hydrogen; or X is not =O; or Y is not =S; or bond (a) is not a double bond; or bonds (b) and (c) are not each single bonds.

In other embodiments, if X is =O, then $R_1$ is a not a hydrogen, or $R_2$ and $R_3$ are not each not a hydrogen; or $R_4$ is not a methyl group; or Y is not =S; or bond (a) is not a double bond; or bonds (b) and (c) are not each single bonds.

If Y is =S, then $R_1$ is a not a hydrogen, or $R_2$ and $R_3$ are not each not a hydrogen; or $R_4$ is not a methyl group; or X is not =O; or bond (a) is not a double bond; or bonds (b) and (c) are not each single bonds.

In yet other embodiments, if bond (a) is a double bond, then $R_1$ is a not a hydrogen, or $R_2$ and $R_3$ are not each not a hydrogen; or $R_4$ is not a methyl group; or X is not =O; or Y is not =S; or bonds (b) and (c) are not each single bonds. If bond (b) is a single bond, then $R_1$ is a not a hydrogen, or $R_2$ and $R_3$ are not each not a hydrogen; or $R_4$ is not a methyl group; or X is not =O; or Y is not =S; bond (a) is not a double bond or bond (c) is not a single bond. If bond (c) is a single bond, then $R_1$ is a not a hydrogen, or $R_2$ and $R_3$ are not each not a hydrogen; or $R_4$ is not a methyl group; or X is not =O; or Y is not =S; bond (a) is not a double bond or bond (b) is not a single bond.

In a second aspect, the invention features a compound in a pharmaceutically acceptable carrier, having the formula:

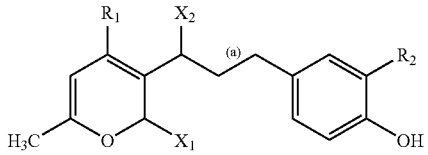

wherein each of $X_1$ and $X_2$ is independently selected from the group consisting of =O, —OH and —H; $R_1$ is selected from the group consisting of hydrogen and hydroxyl; $R_2$ is selected from the group consisting of hydrogen, sulfate, nitro, and halide; and the bond (a) is either a single or double bond.

In a preferred embodiment of the second aspect of the invention, in the compound each of $X_1$ and $X_2$ is =O; $R_1$ is a hydroxyl group; $R_2$ is a nitro group; and the bond (a) is a double bond.

In other embodiments, if $X_1$ is =O, then $X_2$ is not =O; or $R_1$ is not a hydroxyl group; or $R_2$ is a not a nitro group; or the bond (a) is not a double bond. If $X_2$ is =O, then $X_1$ is not =O; or $R_1$ is not a hydroxyl group; or $R_2$ is not a nitro group; or the bond (a) is not a double bond. If $R_1$ is a hydroxyl group, then each of $X_1$ and $X_2$ are not =O; or $R_2$ is a not a nitro group; or the bond (a) is not a double bond. If $R_2$ is a nitro group, then each of $X_1$ and $X_2$ are not =O; or $R_1$ is not a hydroxyl group; or the bond (a) is not a double bond. If the bond (a) is a double bond, then each of $X_1$ and $X_2$ are not =O; or R1 is not a hydroxyl group; or $R_2$ is a not a nitro group; or the bond (a) is not a double bond.

In a third aspect, the invention features a chemical compound in a pharmaceutically acceptable carrier, having the formula:

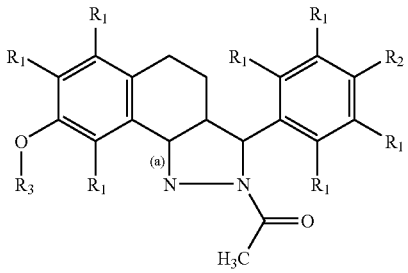

wherein each $R_1$ and $R_2$ is independently selected from the group consisting of hydrogen, amino, halide, and hydroxyl; $R_3$ is selected from the group consisting of hydrogen and methyl; and the bond (a) is either a single or double bond.

In a preferred embodiment of the third aspect of the invention, in the compound each $R_1$ is hydrogen; $R_2$ is fluorine; $R_3$ is a methyl group; and the bond (a) is a double bond.

In other embodiments of the third aspect of the invention, if $R_1$ is a hydrogen, then $R_2$ is not fluorine; or $R_3$ is not a methyl group; or the bond (a) is not a double bond. If $R_2$ is a fluorine, then $R_1$ is not hydrogen; or $R_3$ is a not a methyl group; or the bond (a) is not a double bond. If $R_3$ is a methyl group, then $R_1$ is not hydrogen, or $R_2$ is not fluorine; or the bond (a) is not a double bond. If the bond (a) is a double bond, then $R_1$ is not hydrogen, or $R_2$ is not fluorine; or $R_3$ is not a methyl group.

In a fourth aspect, the invention features a chemical compound in a pharmaceutically acceptable carrier, having the formula:

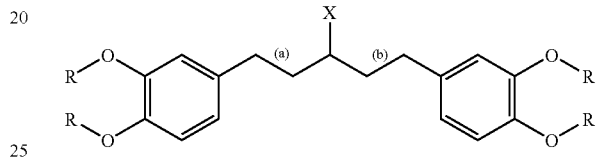

wherein each R is independently selected from the group consisting of H or $CH_3$; the bond (a) is either a single or double bond; the bond (b) is either a single or double bond; and X is selected from the group consisting of =O, —OH and —H.

In a preferred embodiment of the fourth aspect of the invention, in the compound each R is $CH_3$; the bonds (a) and (b) are each a double bond; and X is =O.

In other embodiments of the fourth aspect of the invention, if each R is $CH_3$, then the bonds (a) and (b) are not each a double bond; or X is not =O. If the double bond (a) is a double bond, then each R is not $CH_3$; or the bond (b) is not a double bond; or X is not =O. If the bond (b) is a double bond, then each R is not $CH_3$; or the bond (a) is not a double bond; or X is not =O. If X is =O, then R is not $CH_3$, or the bonds (a) and (b) are not each a double bond.

In a fifth aspect, the invention features a method for decreasing necrosis, involving contacting a cell with a chemical compound having the formula:

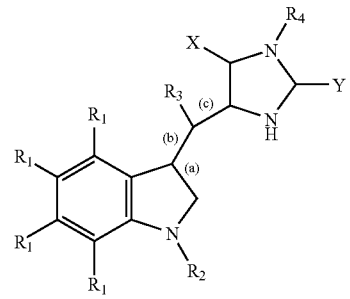

wherein each $R_1$ is independently selected from the group consisting of hydrogen, carboxy, methyl, hydroxyl, methoxyl, amino, and nitro; $R_2$ is selected from the group consisting of hydrogen, alkyl, and acyl; $R_3$ is selected from the group consisting of alkyl, acyl, halogen, hydrogen, or hydroxyl; $R_4$ is selected from the group consisting of methyl, hydroxyl, carboxyl, and linear and branching alkyl groups;

X is selected from the group consisting of =O, —OH and —H; Y is selected from the group consisting of =S and —SR$_5$, where R$_5$ is either hydrogen or an alkyl group; and each of the bonds (a), (b), and (c) independently is either a double or single bond, provided, however, that bond (a) and bond (b) are not both double bonds.

In a preferred embodiment of the fifth aspect of the invention, in the compound each R$_1$ is hydrogen; R$_2$ and R$_3$ are each hydrogen; R$_4$ is a methyl group; X is =O; Y is =S; bond (a) is a double bond; and bonds (b) and (c) are each single bonds.

In another embodiment, the acyl group of R$_1$ or R$_3$ is selected from the group consisting of:

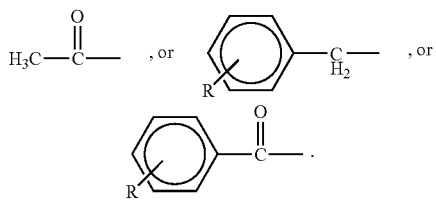

In other embodiments, in the compound if R$_1$ is a hydrogen, then R$_2$ and R$_3$ are not each hydrogen; or R$_4$ is not a methyl group; or X is not =O; or Y is not =S; or bond (a) is not a double bond; or bonds (b) and (c) are not each single bonds. If R$_2$ is a hydrogen, then R$_1$ is a not a hydrogen, or R$_3$ is not a hydrogen; or R$_4$ is not a methyl group; or X is not =O; or Y is not =S; or bond (a) is not a double bond; or bonds (b) and (c) are not each single bonds. If R$_3$ is a hydrogen, then R$_1$ is a not a hydrogen, or R$_2$ is not a hydrogen; or R$_4$ is not a methyl group; or X is not =O; or Y is not =S; or bond (a) is not a double bond; or bonds (b) and (c) are not each single bonds. If R$_4$ is a methyl group, then R$_1$ is a not a hydrogen, or R$_2$ and R$_3$ are not each not a hydrogen; or X is not =O; or Y is not =S; or bond (a) is not a double bond; or bonds (b) and (c) are not each single bonds.

In other embodiments, if X is =O, then R is a not a hydrogen, or R$_2$ and R$_3$ are not each not a hydrogen; or R$_4$ is not a methyl group; or Y is not =S; or bond (a) is not a double bond; or bonds (b) and (c) are not each single bonds. If Y is =S, then R$_1$ is a not a hydrogen, or R$_2$ and R$_3$ are not each not a hydrogen; or R$_4$ is not a methyl group; or X is not =O; or bond (a) is not a double bond; or bonds (b) and (c) are not each single bonds.

In yet other embodiments, if bond (a) is a double bond, then R$_1$ is a not a hydrogen, or R$_2$ and R$_3$ are not each not a hydrogen; or R$_4$ is not a methyl group; or X is not =O; or Y is not =S; or bonds (b) and (c) are not each single bonds. If bond (b) is a single bond, then R$_1$ is a not a hydrogen, or R$_2$ and R$_3$ are not each not a hydrogen; or R$_4$ is not a methyl group; or X is not =O; or Y is not =S; bond (a) is not a double bond or bond (c) is not a single bond. If bond (c) is a single bond, then R$_1$ is a not a hydrogen, or R$_2$ and R$_3$ are not each not a hydrogen; or R$_4$ is not a methyl group; or X is not =O; or Y is not =S; bond (a) is not a double bond or bond (b) is not a single bond.

In a sixth aspect, the invention features a method for decreasing necrosis, involving contacting a cell with a chemical compound having the formula:

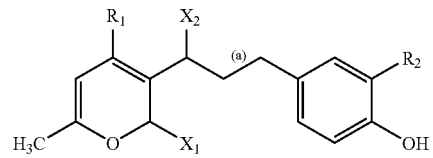

wherein each of X$_1$ and X$_2$ is independently selected from the group consisting of =O, —OH and —H; R$_1$ is selected from the group consisting of hydrogen and a hydroxyl; R$_2$ is selected from the group consisting of hydrogen, sulfate, nitro, and halide; and the bond (a) is either a single or double bond.

In a preferred embodiment of the sixth aspect of the invention, in the compound each of X$_1$ and X$_2$ is =O; R$_1$ is a hydroxyl group; R$_2$ is a nitro group; and the bond (a) is a double bond.

In other preferred embodiments of the sixth aspect of the invention, if X$_1$ is =O, then X$_2$ is not =O; or R$_1$ is not a hydroxyl group; or R$_2$ is a not a nitro group; or the bond (a) is not a double bond. If X$_2$ is =O, then X$_1$ is not =O; or R$_1$ is not a hydroxyl group; or R$_2$ is not a nitro group; or the bond (a) is not a double bond. If R$_1$ is a hydroxyl group, then each of X$_1$ and X$_2$ are not =O; or R$_2$ is a not a nitro group; or the bond (a) is not a double bond. If R$_2$ is a nitro group, then each of X$_1$ and X$_2$ are not =O; or R$_1$ is not a hydroxyl group; or the bond (a) is not a double bond. If the bond (a) is a double bond, then each of X$_1$ and X$_2$ are not =O; or R1 is not a hydroxyl group; or R$_2$ is a not a nitro group; or the bond (a) is not a double bond.

In a seventh aspect, the invention features a method for decreasing necrosis, involving contacting a cell with a chemical compound having the formula:

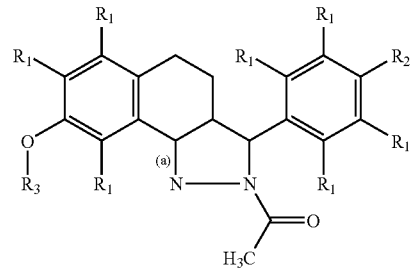

wherein each R$_1$ and R$_2$ is independently selected from the group consisting of hydrogen, amino, halide, and hydroxyl; R$_3$ is selected from the group consisting of hydrogen and methyl; and the bond (a) is either a single or double bond.

In a preferred embodiment of the seventh aspect of the invention, in the compound each R$_1$ is hydrogen; R$_2$ is fluorine; R$_3$ is a methyl group; and the bond (a) is a double bond.

In other embodiments of the seventh aspect of the invention, if R$_1$ is a hydrogen, then R$_2$ is not fluorine; or R$_3$ is not a methyl group; or the bond (a) is not a double bond. If R$_2$ is a fluorine, then R$_1$ is not hydrogen; or R$_3$ is a not a methyl group; or the bond (a) is not a double bond. If R$_3$ is a methyl group, then R$_1$ is not hydrogen, or R$_2$ is not fluorine; or the bond (a) is not a double bond. If the bond (a) is a double bond, then R$_1$ is not hydrogen, or R$_2$ is not fluorine; or R$_3$ is not a methyl group.

In an eighth aspect, the invention features a method for decreasing necrosis, involving contacting a cell with a chemical compound having the formula:

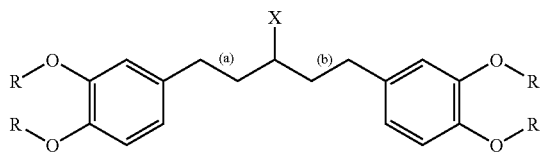

wherein each R is independently selected from the group consisting of H or $CH_3$; the bond (a) is either a single or double bond; the bond (b) is either a single or double bond; and X is selected from the group consisting of =O, —OH and —H.

In a preferred embodiment of the eighth aspect of the invention, in the compound each R is $CH_3$; the (a) and (b) bonds are each a double bond; and X is =O.

In other embodiments of the eighth aspect of the invention, if each R is $CH_3$, then the bonds (a) and (b) are not each a double bond; or X is not =O. If the double bond (a) is a double bond, then each R is not $CH_3$; or the bond (b) is not a double bond; or X is not =O. If the bond (b) is a double bond, then each R is not $CH_3$; or the bond (a) is not a double bond; or X is not =O. If X is =O, then R is not $CH_3$, or the bonds (a) and (b) are not each a double bond.

In a preferred embodiment of any of the fifth, sixth, seventh, or eighth aspects of the invention, the cell is capable of undergoing necrosis in the presence of zVAD-fmk and TNFα. In another preferred embodiment, the cell is capable of undergoing necrosis in the presence of zVAD-fmk and DMSO. In yet another preferred embodiment, the cell is mammalian, such as a human or rodent cell. In yet another preferred embodiment, the cell is a neuron. In still another preferred embodiment, the compound is in a pharmaceutically acceptable carrier.

In a ninth aspect, the invention features a method for treating a condition in a subject, involving the steps of administering a chemical compound having the formula:

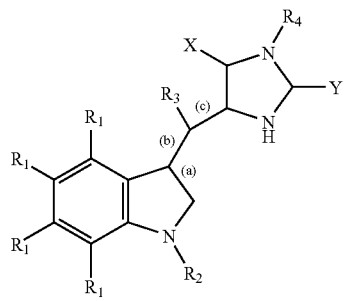

to the subject, in a dosage sufficient to decrease necrosis, wherein each $R_1$ is independently selected from the group consisting of hydrogen, carboxy, methyl, hydroxyl, methoxyl, amino, and nitro; $R_2$ is selected from the group consisting of hydrogen, alkyl, and acyl; $R_3$ is selected from the group consisting of alkyl, acyl, halogen, hydrogen, or hydroxyl; $R_4$ is selected from the group consisting of methyl, hydroxyl, carboxyl, and linear and branching alkyl groups; X is selected from the group consisting of =O, —OH and —H; Y is selected from the group consisting of =S and —$SR_5$, where $R_5$ is either hydrogen or an alkyl group; and each of the bonds (a), (b), and (c) independently is either a double or single bond, provided, however, that bond (a) and bond (b) are not both double bonds.

In a preferred embodiment of the ninth aspect of the invention, in the compound each $R_1$ is hydrogen; $R_2$ and $R_3$ are each hydrogen; $R_4$ is a methyl group; X is =O; Y is =S; bond (a) is a double bond; and bonds (b) and (c) are each single bonds.

In another embodiment, the acyl group of $R_1$ or $R_3$ is selected from the group consisting of:

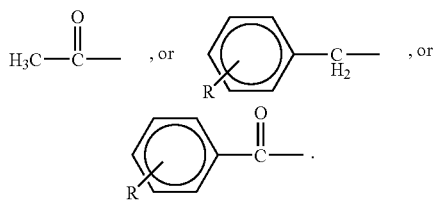

In other embodiments, in the compound if $R_1$ is a hydrogen, then $R_2$ and $R_3$ are not each hydrogen; or $R_4$ is not a methyl group; or X is not =O; or Y is not =S; or bond (a) is not a double bond; or bonds (b) and (c) are not each single bonds. If $R_2$ is a hydrogen, then $R_1$ is a not a hydrogen, or $R_3$ is not a hydrogen; or $R_4$ is not a methyl group; or X is not =O; or Y is not =S; or bond (a) is not a double bond; or bonds (b) and (c) are not each single bonds. If $R_3$ is a hydrogen, then $R_1$ is a not a hydrogen, or $R_2$ is not a hydrogen; or $R_4$ is not a methyl group; or X is not =O; or Y is not =S; or bond (a) is not a double bond; or bonds (b) and (c) are not each single bonds. If $R_4$ is a methyl group, then $R_1$ is a not a hydrogen, or $R_2$ and $R_3$ are not each not a hydrogen; or X is not =O; or Y is not =S; or bond (a) is not a double bond; or bonds (b) and (c) are not each single bonds.

In other embodiments, if X is =O, then $R_1$ is a not a hydrogen, or $R_2$ and $R_3$ are not each not a hydrogen; or $R_4$ is not a methyl group; or Y is not =S; or bond (a) is not a double bond; or bonds (b) and (c) are not each single bonds. If Y is =S, then $R_1$ is a not a hydrogen, or $R_2$ and $R_3$ are not each not a hydrogen; or $R_4$ is not a methyl group; or X is not =O; or bond (a) is not a double bond; or bonds (b) and (c) are not each single bonds.

In yet other embodiments, if bond (a) is a double bond, then $R_1$ is a not a hydrogen, or $R_2$ and $R_3$ are not each not a hydrogen; or $R_4$ is not a methyl group; or X is not =O; or Y is not =S; or bonds (b) and (c) are not each single bonds. If bond (b) is a single bond, then $R_1$ is a not a hydrogen, or $R_2$ and $R_3$ are not each not a hydrogen; or $R_4$ is not a methyl group; or X is not =O; or Y is not =S; bond (a) is not a double bond or bond (c) is not a single bond. If bond (c) is a single bond, then $R_1$ is a not a hydrogen, or $R_2$ and $R_3$ are not each not a hydrogen; or $R_4$ is not a methyl group; or X is not =O; or Y is not =S; bond (a) is not a double bond or bond (b) is not a single bond.

In a tenth aspect, the invention features a method for treating a condition in a subject, involving the steps of administering a chemical compound having the formula:

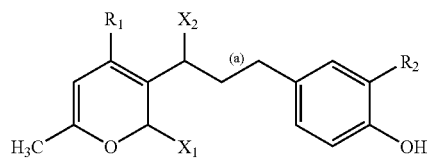

to the subject, in a dosage sufficient to decrease necrosis, wherein each of $X_1$ and $X_2$ is independently selected from the group consisting of =O, —OH and —H; $R_1$ is selected from the group consisting of hydrogen and a hydroxyl; $R_2$ is selected from the group consisting of hydrogen, sulfate, nitro, and halide; and the bond (a) is either a single or double bond.

In a preferred embodiment of the tenth aspect of the invention, in the compound each of $X_1$ and $X_2$ is =O; $R_1$ is a hydroxyl group; $R_2$ is a nitro group; and the bond (a) is a double bond.

In other embodiments of the tenth aspect of the invention, if $X_1$ is =O, then $X_2$ is not =O; or $R_1$ is not a hydroxyl group; or $R_2$ is a not a nitro group; or the bond (a) is not a double bond. If $X_2$ is =O, then $X_1$ is not =O; or $R_1$ is not a hydroxyl group; or $R_2$ is not a nitro group; or the bond (a) is not a double bond. If $R_1$ is a hydroxyl group, then each of $X_1$ and $X_2$ are not =O; or $R_2$ is a not a nitro group; or the bond (a) is not a double bond. If $R_2$ is a nitro group, then each of $X_1$ and $X_2$ are not =O; or $R_1$ is not a hydroxyl group; or the bond (a) is not a double bond. If the bond (a) is a double bond, then each of $X_1$ and $X_2$ are not =O; or R1 is not a hydroxyl group; or $R_2$ is a not a nitro group; or the bond (a) is not a double bond.

In an eleventh aspect, the invention features a method for treating a condition in a subject, involving the steps of administering a chemical compound having the formula:

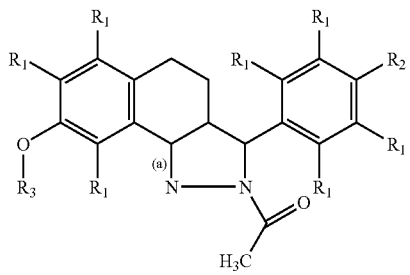

to the subject, in a dosage sufficient to decrease necrosis, wherein each $R_1$ and $R_2$ is independently selected from the group consisting of hydrogen, amino, halide, and hydroxyl; $R_3$ is selected from the group consisting of hydrogen and methyl; and the bond (a) is either a single or double bond.

In a preferred embodiment of the eleventh aspect of the invention, in the compound each $R_1$ is hydrogen; $R_2$ is fluorine; $R_3$ is a methyl group; and the bond (a) is a double bond.

In other embodiments of the eleventh aspect of the invention, if $R_1$ is a hydrogen, then $R_2$ is not fluorine; or $R_3$ is not a methyl group; or the bond (a) is not a double bond. If $R_2$ is a fluorine, then $R_1$ is not hydrogen; or $R_3$ is a not a methyl group; or the bond (a) is not a double bond. If $R_3$ is a methyl group, then $R_1$ is not hydrogen, or $R_2$ is not fluorine; or the bond (a) is not a double bond. If the bond (a) is a double bond, then $R_1$ is not hydrogen, or $R_2$ is not fluorine; or $R_3$ is not a methyl group.

In a twelfth aspect, the invention features a method for treating a condition in a subject, involving the steps of administering a chemical compound having the formula:

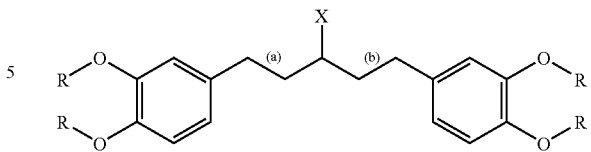

to the subject, in a dosage sufficient to decrease necrosis, wherein each R is independently selected from the group consisting of H or $CH_3$; the bond (a) is either a single or double bond; the bond (b) is either a single or double bond; and X is selected from the group consisting of =O, —OH and —H.

In a preferred embodiment of the twelfth aspect of the invention, in the compound each R is $CH_3$; the (a) and (b) bonds are each a double bond; and X is =O.

In other embodiments of the twelfth aspect of the invention, if each R is $CH_3$, then the bonds (a) and (b) are not each a double bond; or X is not =O. If the double bond (a) is a double bond, then each R is not $CH_3$; or the bond (b) is not a double bond; or X is not =O. If the bond (b) is a double bond, then each R is not $CH_3$; or the bond (a) is not a double bond; or X is not =O. If X is =O, then R is not $CH_3$, or the bonds (a) and (b) are not each a double bond.

In a preferred embodiment of any of the ninth, tenth, eleventh, or twelfth aspects of the invention, the condition is a neurodegenerative disease. Most preferably the neurodegenerative disease is selected from the group consisting of Alzheimer's disease, Huntington's disease, cerebral ischemia, stroke, amyotropic lateral sclerosis, multiple sclerosis, Lewy body disease, Menkes, disease, Wilson disease, Creutzfeldt-Jakob disease, and Fahr disease. In other preferred embodiments, the condition is ischemic brain or heart injury, or head trauma. In another preferred embodiment, the subject is a mammal, such as a human or a rodent.

In a thirteenth aspect, the invention features a method for identifying a compound that decreases necrosis, involving the steps of: providing a cell in which apoptosis is prevented; contacting the cell with a first compound that causes a cell to undergo necrosis; contacting the cell with a second compound; and measuring necrosis relative to a control cell, wherein a decrease in necrosis indicates that the second compound decreases necrosis.

In a preferred embodiment of the thirteenth aspect of the invention, apoptosis is prevented by contacting the cell with zVAD-fmk. In another preferred embodiment, the first compound is TNFα or DMSO.

It will be appreciated that any of the R, X, or Y groups of the compounds of the invention, or of the compounds used in any method of the invention may be alkyl derivatives or contain alkyl linkers.

As used herein, by "decreasing necrosis" is meant reducing the number of cells which undergo necrosis relative to a control cell, receiving a cell death stimulus, such as TNFα/zVAD-fmk or DMSO/zVAD-fmk without a candidate small molecule inhibitor. Preferably necrosis is decreased 10% relative to a control. More preferably necrosis is decreased 50% relative to a control. Most preferably necrosis is decreased 90% relative to a control. Preferably a decrease in necrosis is tested by determining the ATP level in a cell which has received a test compound, such as a compound from a chemical library, and comparing it to the ATP level in a control cell. Necrosis is decreased in a cell treated with a test compound in which the ATP level does not decrease as much as it does in the control cell.

By "test compound" is meant a chemical, be it naturally-occurring or artificially-derived, that is surveyed for its ability to modulate the level of necrosis by employing one of the assay methods described herein. Test compounds may include, for example, peptides, polypeptides, synthesized organic molecules, naturally occurring organic molecules, nucleic acid molecules, and components thereof.

By "cell death" is meant the death of a cell by either apoptosis or necrosis.

As used herein, by "necrosis" is meant caspase-independent cell death characterized by cellular ATP depletion. Preferably the cell is depleted of ATP 10% relative to a control cell, receiving vehicle only (for example, DMSO). More preferably, the cell is depleted of ATP 50% relative to a control cell. Most preferably, the cell is depleted of ATP 90% relative to a control cell. Preferably, necrosis is tested by determining the ATP level in a cell which has received a compound, for example, zVAD-fmk, DMSO, or TNFα, and comparing it to the ATP level in a cell receiving vehicle only. Necrosis occurs in a cell treated with a test compound in which the ATP level decreases relative to the control cell.

Necrosis may be liquifactive, may affect adipose or hepatic tissue, and may be caseous or fibrinoid. A cell may undergo necrosis in response to ischemic cell injury or viral infection.

By "caspase-independent cell death" is meant cell death that occurs when apoptosis is prevented. Apoptosis may be prevented by contacting a cell with a caspase inhibitor such as zVAD-fmk at a concentration sufficient enough that the cell survives when stimulated to undergo apoptosis, for example, by treatment with an apoptosis-promoting drug or ionizing radiation.

By "apoptosis" is meant cell death characterized by any of the following properties: nuclear condensation, DNA fragmentation, membrane blebbing, or cell shrinkage.

By "modulation of intracellular signaling pathways mediated by TNFα" is meant a change in the communication between components of a cell in response to contacting the cell with TNFα. The change may be in the way or duration in which proteins within the cell interact, or the way or duration in which proteins are altered, such as by phosphorylation or dephosphorylation, or in the way or duration in which proteins interact with DNA.

By "modulation of intracellular signaling pathways mediated by DMSO" is meant a change in the communication between components of a cell in response to contacting the cell with DMSO. The change may be in the way or duration in which proteins within the cell interact, or the way or duration in which proteins are altered, such as by phosphorylation or dephosphorylation, or in the way or duration in which proteins interact with DNA.

By "treating" is meant to submit or subject an animal, cell, lysate or extract derived from a cell, or a molecule derived from a cell to a test compound that decreases necrosis.

By "condition" is meant a state of being or feeling. Conditions include, but are not limited to, neurodegenerative disease, stroke, liver disease, pancreatic disease, ischemic brain or heart injury or other ischemic injuries, head trauma, a necrotic ulceration, septic shock, coronary heart disease, gastrointestinal disease, tuberculosis, alteration of blood vessels, viral infection (e.g., HIV infection or AIDS), or conditions associated with HIV infection or AIDS.

By "neurodegenerative disease" is meant a disease characterized by neuronal cell death. Examples of neurodegenerative diseases include, but are not limited to, Alzheimer's disease, Huntington's disease and related polyglutamine expansion diseases, cerebral ischemia, stroke, amyotropic lateral sclerosis, multiple sclerosis, Lewy body disease, Menkes disease, Wilson disease, Creutzfeldt-Jakob disease, and Fahr disease.

By "neuron" is meant a cell of ectodermal embryonic origin derived from any part of the nervous system of an animal. Neurons express well-characterized neuron-specific markers which include neurofilament proteins, MAP2, and class III β-tubulin. Included as neurons are, for example, hippocampal, cortical, midbrain dopaminergic, motor, sensory, sympathetic, septal cholinergic, and cerebellar neurons.

By a "dosage sufficient to decrease necrosis" is meant an amount of a chemical compound or small molecule which when administered to a subject will decrease necrosis. Preferably necrosis is decreased in the subject 10% relative to an untreated subject. More preferably necrosis is decreased in the subject 50% relative to an untreated subject. Most preferably necrosis is decreased in the subject 90% relative to an untreated subject.

As used herein, by "measuring necrosis" is meant determining if a cell is dying through necrosis, in the presence of a compound, compared to a cell which is not in the presence of the compound (control cell). Necrosis can be measured by determining cellular ATP levels, wherein a cell that is undergoing necrosis has a decreased level of cellular ATP compared to a control cell. Necrosis may also be measured by staining with a vital dye, for example, trypan blue, wherein a cell which is necrosing will be stained with the vital dye, and a cell which is not necrosing will not be stained with the dye.

By a "derivative" is meant a structural derivative having a chemical modification of the compound which does not reduce the ultimate level of necrosis, but which does enhance bioavailability, solubility, or stability in vivo or ex vivo or which reduces the toxicity or dosage required. Such modifications are known to those skilled in the field of medicinal chemistry.

The present invention provides a number of advantages. For example, the methods described herein allow for a decrease in cell death occurring through a necrosis pathway. The invention also provides compounds and methods for treating diseases in which necrosis occurs. These compounds and methods can be used to treat conditions such as a neurodegenerative disease, stroke, liver disease, pancreatic disease, ischemic heart or brain injury or other ischemic injuries, head trauma, septic shock, coronary heart disease, gastrointestinal disease, tuberculosis, alteration of blood vessels, viral infection, such as HIV or AIDS, or conditions associated with a viral infection such as HIV or AIDS.

Other features and advantages of the invention will be apparent from the following detailed description and from the claims.

DETAILED DESCRIPTION OF THE INVENTION

Figure 1:
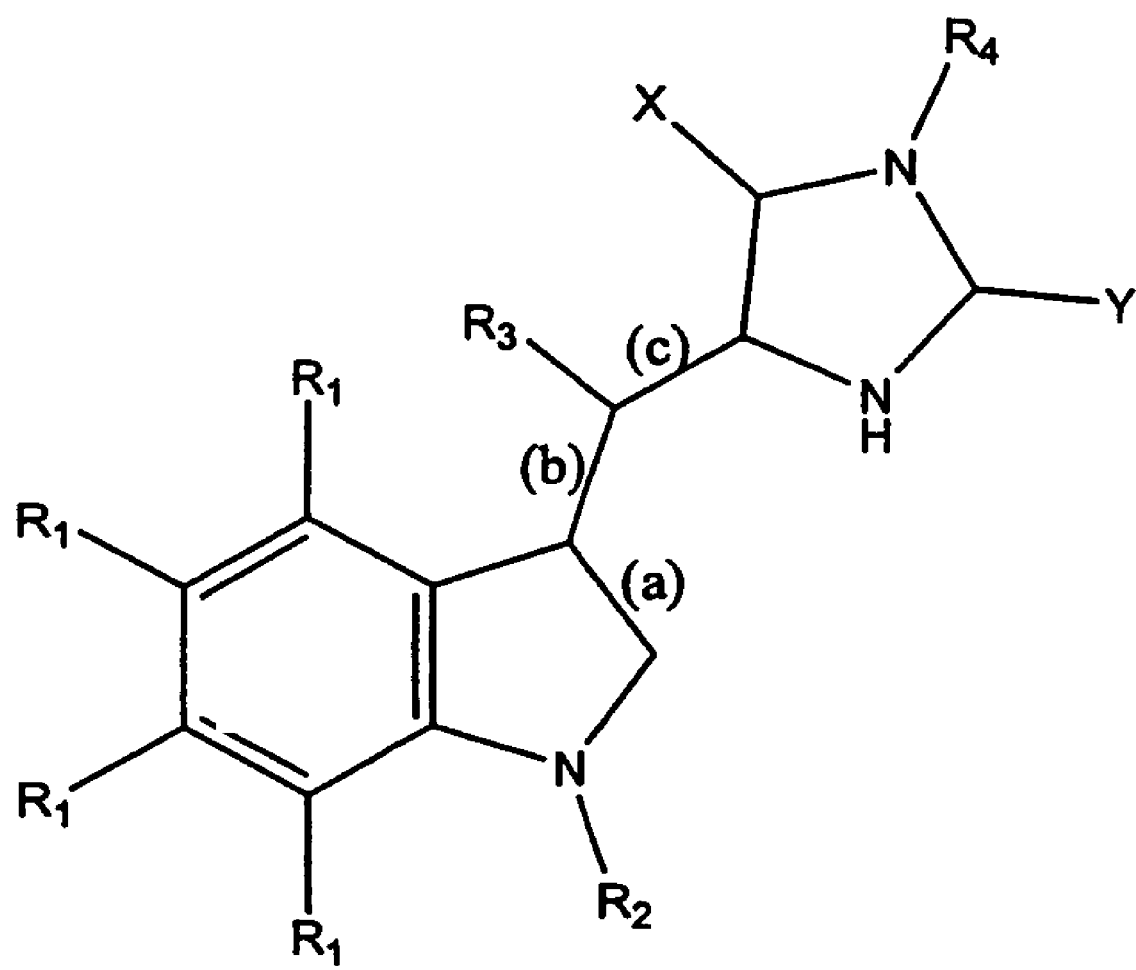
FIG. 1 is a schematic representation of the chemical structure of a molecule which may be used to decrease necrosis. In this chemical structure each $R_1$ is independently selected from the group consisting of hydrogen, methyl, carboxy, hydroxyl, methoxyl, amino, and nitro; $R_2$ is selected from the group consisting of hydrogen, alkyl, and acyl; $R_3$ is selected from the group consisting of alkyl, acyl, halogen, hydrogen, or hydroxyl; $R_4$ is selected from the group consisting of methyl, hydroxyl, carboxyl, and linear and branching alkyl groups; X is selected from the group consisting of =O, —OH and —H; Y is selected from the group consisting of =S and —SR$_5$, where R$_5$ is either hydrogen or an alkyl group; and each of the bonds (a), (b), and (c) independently is either a double or single bond, provided, however, that bond (a) and bond (b) are not both double bonds.
Figure 2:
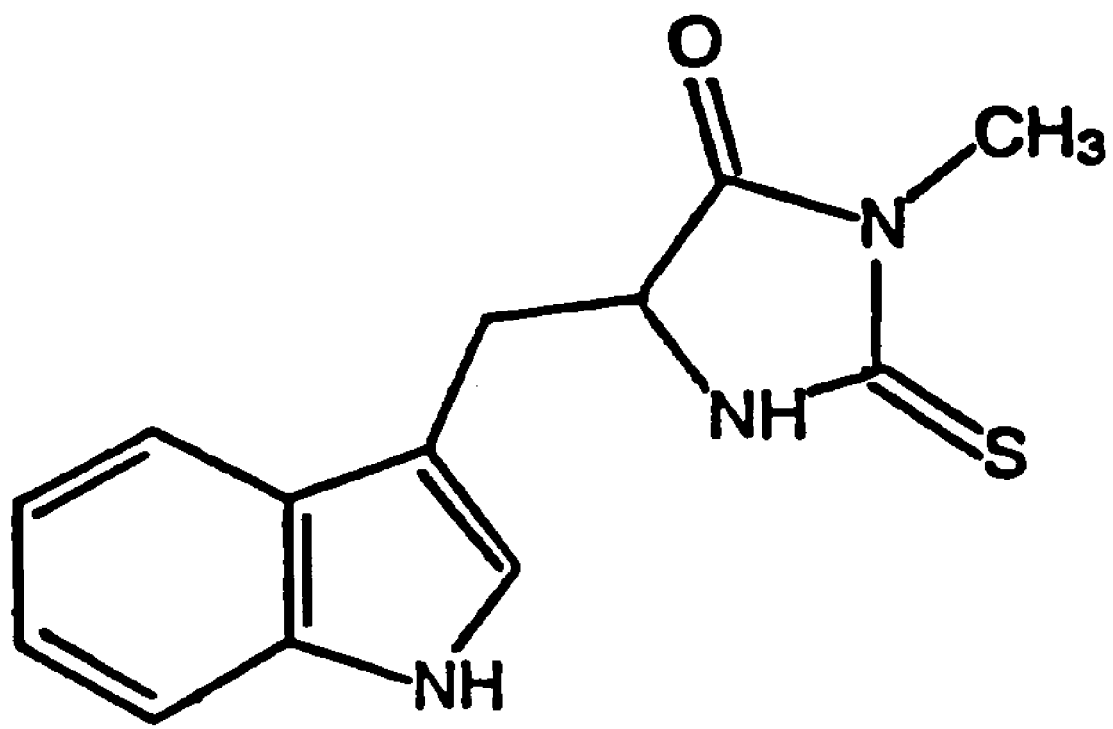
FIG. 2 is a schematic representation of the chemical structure of chemical compound ID number 115807 from the ChemBridge chemical compound library.
Figure 3:
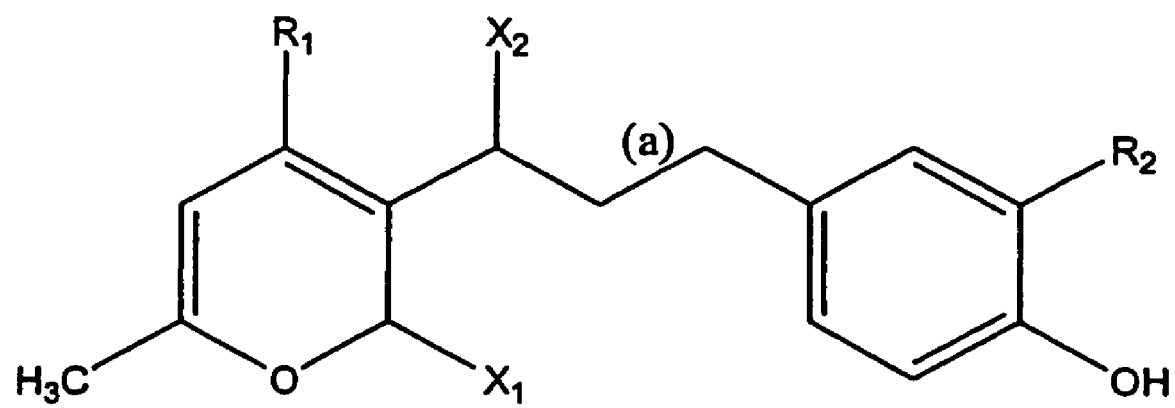
FIG. 3 is a schematic representation of the chemical structure of a molecule which may be used to decrease necrosis. In this chemical structure, each of X$_1$ and X$_2$ is independently selected from the group consisting of =O, —OH and —H; R$_1$ is selected from the group consisting of hydrogen and a hydroxyl; R$_2$ is selected from the group consisting of hydrogen, sulfate, nitro, and halide; and the bond (a) is either a single or double bond.
Figure 4:
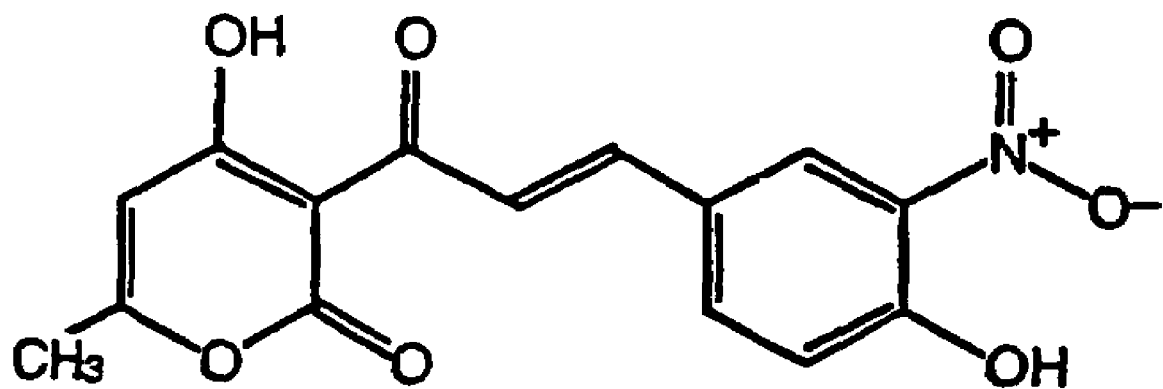
FIG. 4 is a schematic representation of the chemical structure of chemical compound ID number 115681 from the ChemBridge chemical compound library.

Described herein are methods for decreasing necrosis, as well as for treating a condition in a subject. Techniques for carrying out the methods of the invention are now described in detail.

Identification of Chemical Compounds that Decrease Cell Necrosis

Assays that measure cell necrosis may be used to facilitate the identification of molecules that decrease necrosis induced by stimuli, such as zVAD-fmk/TNFα. In one approach, zVAD-fmk is added to the culture media of cells at high density (for example, 5×10$^5$ or 7.5×10$^5$ cells/ml), which are capable of undergoing necrosis in response to zVAD-fmk/TNFα. Candidate molecules, for example, chemical compounds from the ChemBridge chemical library are added, in varying concentrations to the cells, and the cells are then exposed to TNFα.

The occurrence of necrosis of the treated cells is then measured, for example, by measuring the cellular ATP level of the cells exposed to zVAD-fmk/TNFα (Crouch et al. J. Immunol. Methods 160:81-8, 1993; Storer et al. Mutat. Res. 368:59-101, 1996; and Cree et al. Toxicol. In Vitro 11:553-556, 1997). The level of necrosis in the presence of the candidate molecule is compared to the level of necrosis in the absence of the candidate molecule, all other factors (e.g., cell type and culture conditions) being equal. The importance of zVAD-fmk in the invention is to block cell death that may occur by apoptosis, so that cell death by necrosis can be fully unmasked.

In a second approach, a cell may be exposed to a candidate molecule that decreases necrosis at the same time it is exposed to either zVAD-fmk or TNFα. In a third approach, a cell may be exposed to zVAD-fmk and TNFα first, and then to a candidate compound. The level of necrosis that occurs following each of these approaches is measured as described above.

The effect of candidate molecules on necrosis induced by cell death stimuli, for example, zVAD-fmk/TNFα or zVAD-fmk/DMSO, may also be measured by other methods, for example, vital dye staining, using dyes such as trypan blue or acridine orange/ethidium bromide.

Compounds that decrease necrosis may be purified or substantially purified, or may be one component of a mixture of compounds, such as a pool of chemical compounds. In an assay of a mixture of compounds, the occurrence of necrosis is tested against progressively smaller subsets of the compound pool (e.g., produced by standard purification techniques such as HPLC or FPLC) until a single compound or minimal number of effective compounds is demonstrated to decrease necrosis. A molecule that promotes a decrease in necrosis induced by zVAD-fmk/TNFα is considered particularly useful in the invention; such a molecule may be used, for example, as a therapeutic to decrease necrosis, in a patient with a condition in which necrosis occurs, such as a neurodegenerative disease.

Chemical compounds that are found, by the methods described above, to effectively decrease necrosis induced, for example, by zVAD-fmk/TNFα in an in vitro system may be tested further in animal models. Particularly useful animal models include mouse and rat models of cell death, ischemic brain or heart injury or other ischemic injuries, head trauma, neurodegenerative diseases, coronary heart disease, and septic shock. Examples of such models include SOD or Huntington's disease gene transgenic mice, and other known models, such as those described by Li et al. (Hum. Mol. Genet. 8:1227-12236, 1999), Levine et al. (Neurosci. Res. 58:515-532, 1999), Vukosavic et al. (J. Neurochem. 73:2460-2468, 1999), Gruney (J. Neurol. Sci. 152 suppl. 1:S67-73, 1997), Deshmukh et al. (Am. J. Physiol. 273 (4 Pt 1):C1130-1135, 1997), and Isibashi et al. (J. Immunol. 163:5666-5677, 1999). Compounds which demonstrate an ability to decrease necrosis in in vivo models may be used as therapeutics to prevent necrosis, as appropriate.

Identification of Chemical Compounds that Decrease zVAD-fmk/DMSO Induced Cell Necrosis Methods for the identification of chemical compounds that decrease cell necrosis induced, for example, by zVAD-fmk/DMSO at a low cell density (e.g., 1×10$^5$ cells/ml) is achieved essentially as described above, except, the inducer of necrosis is zVAD-fmk/DMSO, rather than zVAD-fmk/TNFα.

Structural Derivatives of Chemical Compounds that Decrease Necrosis

The small molecules identified to decrease necrosis may be structurally modified and subsequently used to decrease necrosis, or to treat a subject with a condition in which necrosis occurs. For example, the small molecules may be modified by any of the following processes: reduction of aliphatic double bonds; reduction of aliphatic ketones; substitution of nitro groups with protons, halides, or sulfates; reduction of C=O double bonds in flavone rings; elimination of oxygens attached to flavone rings; substitution of methoxyl groups with hydroxyl groups; attachment of hydroxyl and amino groups to benzyl rings; reduction of C=N double bonds; elimination of a fluoride or its substitution with a hydroxyl or other halide group; substitution of a hydrogen with an alkyl group; introduction of hydroxyl, methoxyl, amino, and nitro groups into the benzyl ring; reduction of the double bond in the position 2 of the indol; introduction of double bonds in the linker between indol and hydantoin moieties; reduction or alkylation of the thiourea moiety; reduction, alkylation, or acylation of the indol amino group; substitution of the hydantoin 3-methyl group with linear and branching alkyl groups of varying length, and with hydroxyl, methyl, or carboxyl functionalities; and reduction of the hydantoin ketone moiety.

The chemical compounds that decrease necrosis may be modified by one of the above processes or various combinations of the above processes. The methods used to generate structural derivatives of the small molecules that decrease necrosis are readily known to those skilled in the fields of organic and medicinal chemistry.

Therapy

A compound identified as capable of decreasing necrosis, using any of the methods described herein, may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a disease in which necrosis occurs. Administration may begin before the patient is symptomatic.

Any appropriate route of administration may be employed. For example, the therapy may be administered either directly to the site of a predicted cell death event (for example, by injection) or systemically (for example, by any conventional administration technique). Administration of the compound may also be parenteral, intravenous, intraarterial, subcutaneous, intramuscular, intracranial, intraorbital, ophthalmalic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols. The dosage of the therapeutic compounds in a pharmaceutically-acceptable formulation depends on a number of factors, including the size and health of the individual patient. The dosage to deliver may be determined by one skilled in the art.

Methods well known in the art for making formulations are found, for example, in "Remington: The Science and Practice of Pharmacy" ((19th ed.) ed. A. R. Gennaro A R., 1995, Mack Publishing Company, Easton, Pa.). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds that decreases necrosis include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The methods and compounds of the present invention may be used to treat a number of diseases, as described above. Such methods and compounds may be particularly useful in treating ischemic brain or heart injury or head trauma. These diseases would be excellent targets of such therapies, as necrosis occurs in them.

If desired, treatment with a compound identified according to the methods described above, may be combined with more traditional therapies for a disease characterized by cell death, such as tacrine hydrochloride for the treatment of Alzheimer's disease, or interferon β-1a for the treatment of multiple sclerosis.

Preventative Anti-Necrosis Therapy

In a patient diagnosed with a heart disease (e.g., coronary heart disease or ischemic heart injury) or degenerative disease (e.g., a neurodegenerative disease, such as Alzheimer's disease or Huntington's disease), any of the above therapies may be administered before the occurrence of the disease phenotype. In particular, compounds shown to decrease necrosis may be administered by any standard dosage and route of administration (as described above).

The methods of the instant invention may be used to decrease necrosis of a cell or to treat disorders described herein in any mammal, for example, humans, domestic pets, or livestock.

The following examples are provided to illustrate the invention. These examples should not be construed as limiting.

EXAMPLE 1

Cells Undergo Necrosis in Response to zVAD-fmk and TNFα

The cell lines U-937 and BALB/c 3T3 were assayed for the occurrence of necrosis in response to the combined treatment of zVAD-fmk, a caspase inhibitor; and TNFα, a cell death stimulator. The cells ($5\times10^5$ cells/ml) were exposed to zVAD-fmk (100 μM) and human TNFα (40 ng/ml) for 72 hours. Induction of necrosis was assayed by measuring the cellular ATP levels in response to TNFα (Crouch et al., supra, Storer et al. supra, and Cree et al. supra). Cells which underwent necrosis exhibited decreased cellular ATP levels relative to controls cells which received no treatment, zVAD-fmk (100 μM) alone, or human TNFα (40 ng/ml) alone. It was found that the cells underwent necrosis in response to treatment with zVAD-fink and TNFα. The cells were also observed morphologically for the occurrence of apoptosis or necrosis, for example, by analyzing the cells for membrane blebbing and nuclear condensation.

EXAMPLE 2

Identification of Small Molecules that Decrease Necrosis

The U-937 cell line was used to screen a library of 16,000 small molecule chemical compounds for a compound's ability to decrease necrosis induced by exposure of the cell to zVAD-fmk and TNFα. The library of chemical compounds used in this screen were from ChemBridge (ChemBridge Corporation, San Diego Calif.).

In a primary screen, U-937 cells ($5\times10^5$ or $7.5\times10^5$ cells/ml) were first exposed to zVAD-fmk (100 μM). Thirty minutes later the same cells were exposed to a chemical compound from the library (5 mg/ml, dissolved in 0.1-0.5 μl of DMSO, giving a final DMSO concentration of 0.3% to 1.5%). After an additional thirty minutes, TNFα (40 ng/ml) was added to the cell culture medium. The cells were then incubated at 37° C. for 72 hours, and were then assayed for cellular ATP levels. Compounds which did not prevent a decrease in cellular ATP levels were compounds which did not prevent necrosis in response to treatment of the cell with zVAD-fmk and TNFα. Compounds which maintained cellular ATP levels were compounds which blocked necrosis triggered by zVAD-fmk and TNFα.

As a result of the primary screen, 50 chemical compounds from the library were identified to decrease necrosis induced by zVAD-fmk and TNFα. These compounds were selected for a second round of screening for compounds that decrease necrosis induced by zVAD-fmk and TNFα.

In a secondary screen, the compounds identified from the first screen, above, to decrease necrosis induced by zVAD-fmk and TNFα were assayed for their potency. Serial dilution of each chemical compound was performed and the compounds were administered to U-937 cells, as per the primary screen. The concentrations of each compound were 70 μM, 23 μM, 8 μM, and 2.5 μM. The level of necrosis occurring in response to zVAD-fmk, TNFα, and the various concentrations of chemical compounds was assayed as described above for the primary screen.

As a result of the secondary screen, four chemical compounds from the ChemBridge library: 115807, 115681, 210227, and 215686 were identified to decrease necrosis in response to exposure of the cell to zVAD-fmk and TNFα.

EXAMPLE 3

Cells Are Protected From Necrosis Upon Exposure to zVAD-fmk and DMSO

Exposure of low density U-937 cells ($1\times10^5$ cells/ml) to zVAD-fmk (100 μM) and DMSO (0.5%) for 72 hours results in cell death by necrosis. The compounds identified to decrease cell necrosis triggered by zVAD-fmk and TNFα, compounds 115807, 115681, 210227, and 215686 from the ChemBridge chemical library, were also evaluated for their ability to decrease cell necrosis induced by zVAD-fmk and DMSO. The cells ($1\times10^5$ cells/ml) were first exposed to zVAD-fmk, and then thirty minutes later to the above-identified small molecules that decrease necrosis. After an additional 30 minutes, the cells were exposed to DMSO. Seventy-two hours after exposure to the compounds, cellular ATP levels were measured, as described above. All four chemical compounds that decreased necrosis induced by zVAD-fmk/TNFα also decreased necrosis induced by zVAD-fmk/DMSO.

EXAMPLE 4

The Role of Fas-associated Death Domain Protein in zVAD-fmk/TNFα- or zVAD-fmk/DMSO-induced Necrosis A cell expressing a dominant negative form of the protein Fas-associated death domain (FADD) can also prevent a cell from undergoing necrosis in response to treatment with zVAD-fmk/TNFα- or zVAD-fmk/DMSO. Jurkat cells were stably transfected with a FADD-FKBP fusion construct (Kawahara A. et al. J. Cell Biol. 143(5):1353-60, 1998). Normally such cells undergo apoptosis when FADD is multimerized. However, these cells, in the presence of the caspase inhibitor zVAD-fmk, are protected from apoptosis, and instead undergo necrosis, thus establishing the dependence of apoptosis in this system on caspase activity and induction of necrosis in the absence of caspases.

The stably transfected Jurkat cells (500,000 cells/ml) were treated with 100 nM of FKBP dimerizer (Arraid Pharmaceuticals; used to stimulate FADD multimerization) in the presence of 100 μM of zVAD-fmk (pre-treated for 1 hour) and compounds from the library identified to decrease necrosis (dissolved in DMSO to give a final DMSO concentration of 0.5%; added 30 minutes after zVAD-fmk) for 48 hours. Cell viability was then assessed by measuring cellular ATP levels. The small molecules provided protection from necrosis induced in the presence of zVAD-fmk, but not from apoptosis induced by FADD dimerization in the absence of zVAD-fmk. These results indicate that FADD may be involved in mediating necrosis in response to zVAD-fmk/TNFα- or zVAD-fmk/DMSO. It is possible that the small molecules that decrease necrosis may function by interacting with FADD and disrupting FADD's normal function of promoting necrosis upon treatment of a cell with zVAD-fmk/TNFα- or zVAD-fmk/DMSO.

EXAMPLE 5

Identification of Intracellular Targets of Small Molecules that Decrease Necrosis Molecules within a cell that interact with the small molecule compounds that decrease necrosis can be identified using a number of different strategies. Each strategy involves detecting interactions between various proteins from a cell and a small molecule that decreases necrosis, identified according to the methods described above. To identify proteins that interact with a small molecule that decreases necrosis, the small molecule may be bound to a bead, using methods known to those skilled in the art. Each strategy should be carried out using proteins from cells which have been exposed to zVAD-fmk/TNFα- or zVAD-fmk/DMSO.

In one strategy, the signaling complex containing FADD, among other proteins, may be immunoprecipitated, using standard techniques known to those skilled in the art. This complex may then be added to the beads containing the desired small molecule compound that decreases necrosis. Proteins that interact with the small molecule that decreases necrosis may be identified by Western blot detection of proteins contained in the complex, or other techniques known to those skilled in the field of molecular biology. Any detected binding interactions indicate that the target of the small molecule that decreases necrosis is present in the immunoprecipitated FADD complex.

In a second strategy for identifying targets of a small molecule that decreases necrosis, a cell may be fractionated, and the various fractionated pools may be assayed for interaction with the chemical compound using standard molecular biology techniques. A pool of proteins which interacts with the small molecule that decreases necrosis indicates that the pool contains a protein that is a target of the small molecule that decreases necrosis. The target of the small molecule that decreases necrosis may be isolated using techniques known to those skilled in the art.

A third strategy involves small pool expression screening systems. Targets of a small molecule that decreases necrosis can be identified from any cell in which the small molecule protects cells from necrosis triggered by zVAD-fmk/TNFα- or zVAD-fmk/DMSO. This method for identifying targets of small molecules that decrease necrosis can be done, for example, according to the methods of Lustig et al. (Methods in Enzymology 283:83-99, 1997). In this method a cDNA library is made from a desired cell line, or any other desired source. The cDNA library is then divided into pools of 100 clones, and the cDNAs are transcribed and translated to form proteins pools for the detection of interactions between a protein and a small molecule that decreases necrosis. Interactions between the small molecules that decrease necrosis and pools of library proteins can be detected using standard molecular biology techniques, for example, SDS-PAGE.

EXAMPLE 6

Structural Derivatives of Small Molecules that Decrease Necrosis

The following modifications of the small molecules that decrease necrosis may be made and evaluated for their efficacy in decreasing necrosis, for example, that induced by zVAD-fmk/TNFα or zVAD-fmk/DMSO.

The chemical compound 115807 may be modified by the introduction of a hydroxyl, methyl, carboxy, methoxyl, amino or nitro group into the benzyl ring (for example, at any or all of the $R_1$ positions of FIG. 1). Double bonds may be introduced in the linker between indol and hydantoin moieties (for example, in FIG. 1, bonds (a), (b), or (c) may be double bonds, provided that not both bonds (a) and (b) are double bonds). The thiourea moiety may be reduced or alkylated (for example, the moiety may be —SH or $SR_5$, wherein $R_5$ is an alkyl group). The indol amino group may be reduced, alkylated, or acylated (for example, in FIG. 1, $R_2$ may be CH3, $CH_3(CH_2)_n$, where n is between 1 and 4 and, HOOC—$(CH_2)_n$, where n is between 1 and 4,

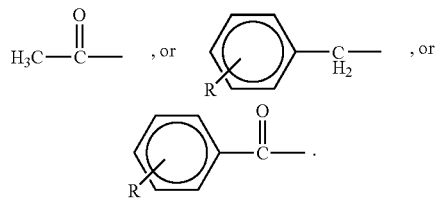

In addition, the hydantoin 3-methyl group may be substituted with linear or branching alkyl groups of varying length, and with hydroxyl, methyl, or acyl functionalities (for example the following groups ma be present at the R4 position of FIG. 1; $CH_3$, $CH_3(CH_2)_n$ where n is between 1 and 4, OH, or HOOC—$(CH_2)_n$—, wherein n is between 1 and 4. In addition, the linker $CH_2$ group between the indol and hydantoin moieties can be alkylated, acylated, halogenated, or hydroxylated (for example, in FIG. 1, $R_4$ may be $CH_3$, $CH_3(CH_2)_n$, where n is between 1 and 4, HOOC—$(CH_2)_n$, where n is between 1 and 4,

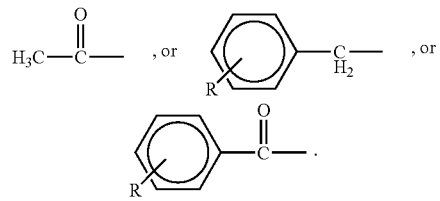

Lastly, the hydantoin ketone moiety may be reduced to a hydroxyl group or a hydrogen.

Figure 5:
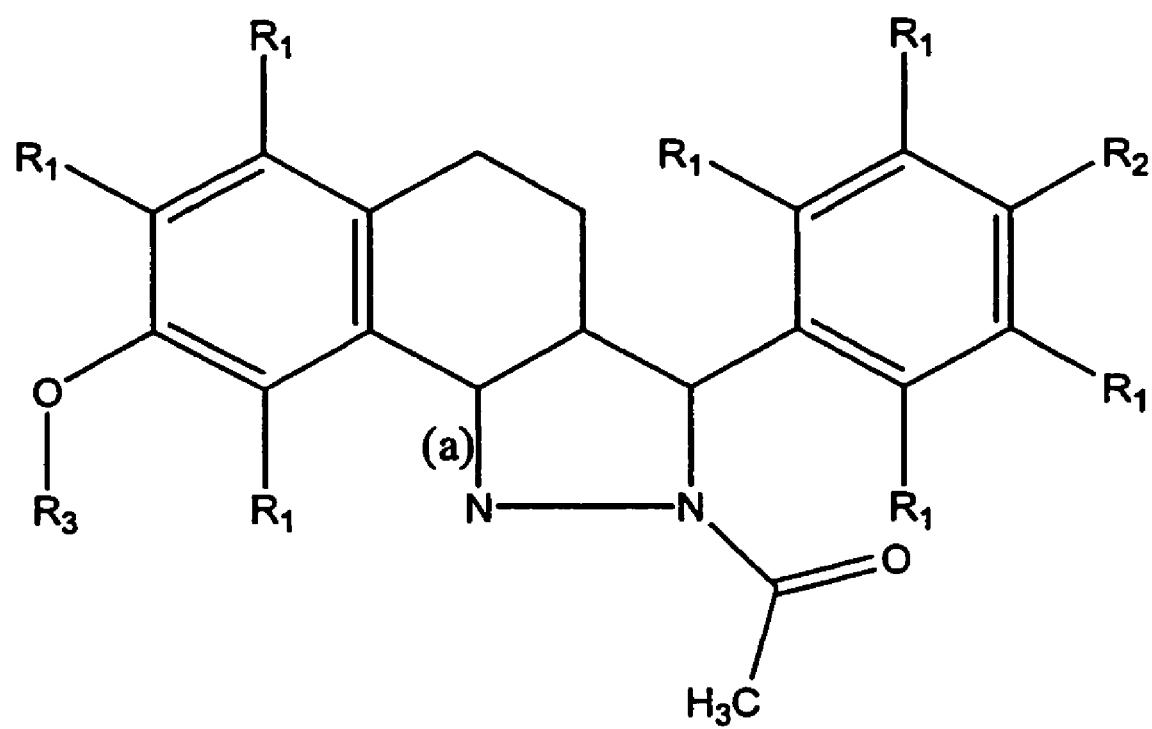
FIG. 5 is a schematic representation of the chemical structure of a molecule which may be used to decrease necrosis. In this chemical structure each R$_1$ and R$_2$ is independently selected from the group consisting of hydrogen, amino, halide, and hydroxyl; R$_3$ is selected from the group consisting of hydrogen and methyl; and the bond (a) is either a single or double bond.
Figure 6:
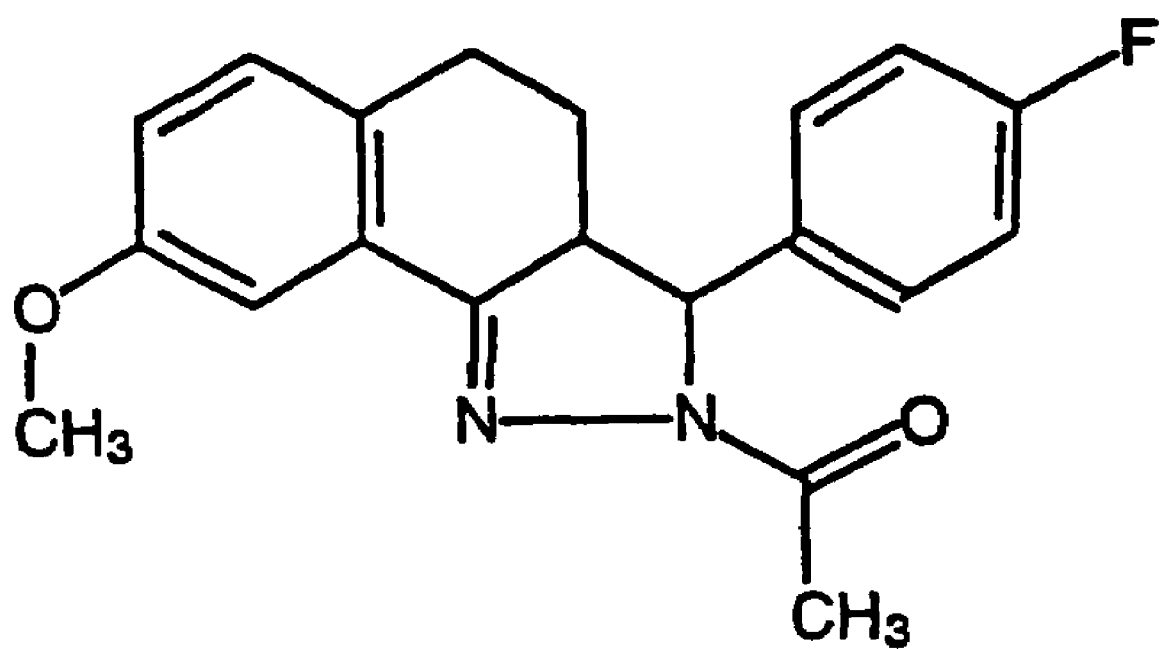
FIG. 6 is a schematic representation of the chemical structure of chemical compound ID number 210227 from the ChemBridge chemical compound library.
Figure 7:
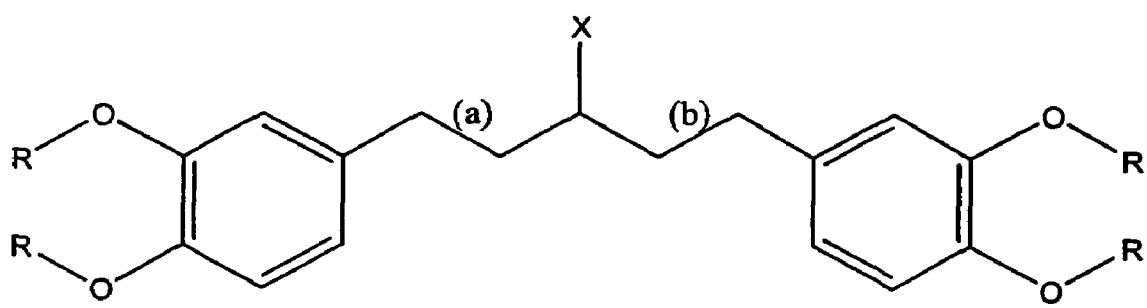
FIG. 7 is a schematic representation of the chemical structure of a molecule which may be used to decrease necrosis. In this chemical structure each R is independently selected from the group consisting of H or CH$_3$; the bond (a) is either a single or double bond; the bond (b) is either a single or double bond; and X is selected from the group consisting of =O, —OH and —H.
Figure 8:
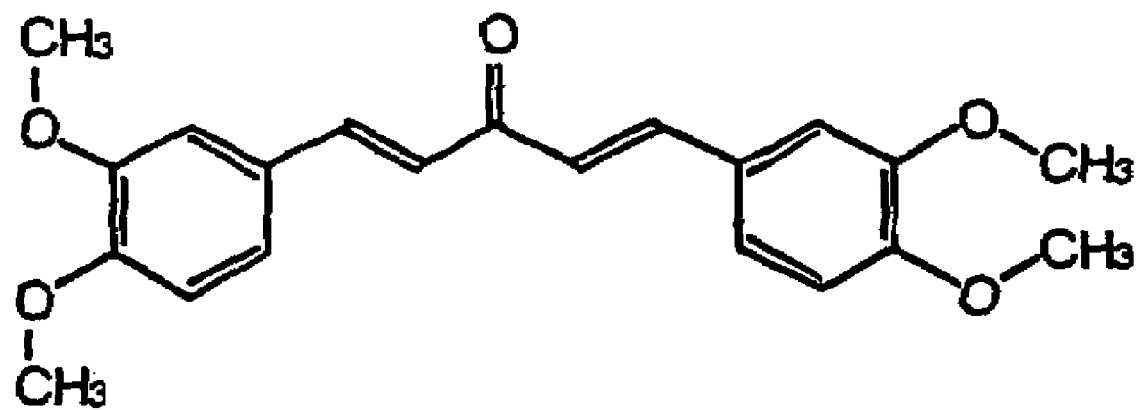
FIG. 8 is a schematic representation of the chemical structure of chemical compound ID number 215686 from the ChemBridge chemical compound library.

The chemical compound 210227 may be modified by the attachment of a halide, or hydroxyl or amino groups to either or both of the benzyl rings (for example, in the $R_1$ or $R_2$ positions of FIG. 5). The C=N double bond may be reduced, or the fluoride may be eliminated or substituted with a hydroxyl group or other halide.

The chemical compound 215686 may be modified by reducing the two central aliphatic double bonds, together, or each one individually. The ketone may also be reduced, or the methoxyl groups may be substituted with hydroxyl groups, each individually, or together.

The chemical compound 115681 may be modified in the following ways. The aliphatic double bond or the aliphatic ketone may be may be reduced. The nitro group may be substituted with a proton, halide, or sulfate. The C=O double bond in the flavone ring may be reduced. Either one or two of the oxygens attached to the flavone may also be eliminated.

What is claimed is:

1. A method for decreasing necrosis, said method comprising contacting a cell with a compound having the formula:

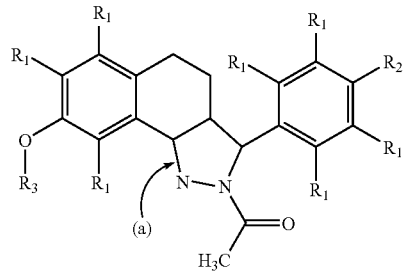

wherein
each $R_1$ is hydrogen;
$R_2$ is fluorine;
$R_3$ is a methyl group; and
the bond (a) is a double bond.

2. The method of claim 1, wherein said cell is capable of undergoing necrosis in the presence of zVAD-fmk and TNFα.

3. The method of claim 1, wherein said cell is capable of undergoing necrosis in the presence of zVAD-fmk and DMSO.

4. The method of claim 1, wherein said cell is mammalian.

5. The method of claim 4, wherein said cell is human.

6. The method of claim 4, wherein said cell is a neuron.

7. The method of claim 4, wherein said cell is a rodent cell.

* * * * *

UNITED STATES PATENT AND TRADEMARK OFFICE
CERTIFICATE OF CORRECTION

| | | |
|---|---|---|
| PATENT NO. | : 7,253,201 B2 | Page 1 of 1 |
| APPLICATION NO. | : 10/880377 | |
| DATED | : August 7, 2007 | |
| INVENTOR(S) | : Junying Yuan et al. | |

It is certified that error appears in the above-identified patent and that said Letters Patent is hereby corrected as shown below:

Column 1, lines 14-20: Please remove the following paragraph:

"STATEMENT AS TO FEDERALLY SPONSORED RESEARCH
   This invention was made in part with Government funding, and the Government therefore has certain rights in the invention."

Signed and Sealed this

Twentieth Day of November, 2007

JON W. DUDAS
*Director of the United States Patent and Trademark Office*